(12) United States Patent
Mahmood

(10) Patent No.: US 11,909,230 B2
(45) Date of Patent: Feb. 20, 2024

(54) WEARABLE ARTICLE AND ELECTRONICS ARRANGEMENT FOR TRANSFERRING POWER

(71) Applicant: Prevayl Innovations Limited, Manchester (GB)

(72) Inventor: Tahir Mahmood, Manchester (GB)

(73) Assignee: Prevayl Innovations Limited, Manchester (GB)

( * ) Notice: Subject to any disclaimer, the term of this patent is extended or adjusted under 35 U.S.C. 154(b) by 0 days.

(21) Appl. No.: 17/765,724

(22) PCT Filed: Oct. 28, 2020

(86) PCT No.: PCT/GB2020/052722
§ 371 (c)(1),
(2) Date: Mar. 31, 2022

(87) PCT Pub. No.: WO2021/084245
PCT Pub. Date: May 6, 2021

(65) Prior Publication Data
US 2022/0407367 A1    Dec. 22, 2022

(30) Foreign Application Priority Data

Oct. 29, 2019    (GB) ..................... 1915658

(51) Int. Cl.
*H02J 50/80* (2016.01)
*H02J 50/12* (2016.01)
(Continued)

(52) U.S. Cl.
CPC .............. *H02J 50/80* (2016.02); *A61B 1/002* (2013.01); *H02J 50/12* (2016.02); *H02J 50/40* (2016.02)

(58) Field of Classification Search
CPC . H02J 50/80; H02J 50/12; H02J 50/40; A61B 1/002
(Continued)

(56) References Cited

U.S. PATENT DOCUMENTS 8,862,235 B1    10/2014    Stover et al.
9,721,011 B1    8/2017    Abeloe et al.
(Continued)

FOREIGN PATENT DOCUMENTS

CN    102752681 A    10/2012
CN    105429663 A    3/2016
(Continued)

OTHER PUBLICATIONS

GB Search Report of GB Application No. 2212037.2 dated Nov. 22, 2022.
(Continued)

*Primary Examiner* — Alfonso Perez Borroto
(74) *Attorney, Agent, or Firm* — Haley Guiliano LLP

(57) ABSTRACT

The wearable article (11) comprises a power source (111) and a processor (112). The processor (112) determines whether a power transfer condition is satisfied. In response, the processor (112) is arranged to control the wearable article (11) to transfer power from the power source (111) to an electrical load of an external apparatus. The wearable article (11) may comprise an interface element (114) for forming an electrical connection with the externa apparatus. The wearable article (11) may comprise a power transmitter (113) for beaming electromagnetic energy to the external apparatus. The wearable article (11) may be a garment.

20 Claims, 5 Drawing Sheets

(51) Int. Cl.
*H02J 50/40* (2016.01)
*A61B 1/002* (2006.01)

(58) Field of Classification Search
USPC .......................................................... 307/31
See application file for complete search history.

(56) References Cited

U.S. PATENT DOCUMENTS

| | | | |
|---|---|---|---|
| 9,721,077 | B1 | 8/2017 | Daniel |
| 9,837,846 | B2* | 12/2017 | Partovi .................. H02J 50/90 |
| 2002/0124295 | A1 | 9/2002 | Fenwick et al. |
| 2007/0109208 | A1 | 5/2007 | Turner |
| 2009/0168088 | A1* | 7/2009 | Rosenblatt ............. B65D 75/52 358/1.12 |
| 2009/0270951 | A1* | 10/2009 | Kallmyer ............. A61N 1/3787 607/61 |
| 2010/0114143 | A1* | 5/2010 | Albrecht ............... A61F 5/0046 606/191 |
| 2010/0146308 | A1* | 6/2010 | Gioscia .................. H02J 50/90 307/104 |
| 2012/0012630 | A1* | 1/2012 | Lui ........................ A41F 9/002 224/660 |
| 2012/0050153 | A1 | 3/2012 | Dvortsov et al. |
| 2012/0153740 | A1 | 6/2012 | Soar |
| 2012/0206097 | A1 | 8/2012 | Soar |
| 2013/0093389 | A1 | 4/2013 | Partovi |
| 2014/0116085 | A1 | 5/2014 | Lam |
| 2014/0135593 | A1 | 5/2014 | Jayalth et al. |
| 2014/0151079 | A1 | 6/2014 | Furui et al. |
| 2014/0225786 | A1 | 8/2014 | Lyons et al. |
| 2014/0336896 | A1 | 11/2014 | Udaka et al. |
| 2014/0353300 | A1 | 12/2014 | Swiatek et al. |
| 2015/0102879 | A1 | 4/2015 | Jacobs et al. |
| 2015/0349571 | A1 | 12/2015 | Wagman et al. |
| 2015/0364938 | A1 | 12/2015 | Lapetina et al. |
| 2016/0062417 | A1 | 3/2016 | Chu et al. |
| 2016/0071397 | A1 | 3/2016 | Logan et al. |
| 2016/0091922 | A1 | 3/2016 | Nazzaro et al. |
| 2016/0134961 | A1 | 5/2016 | Shaffer |
| 2016/0135743 | A1 | 5/2016 | Cobbett et al. |
| 2016/0218414 | A1 | 7/2016 | Samardzija et al. |
| 2016/0266606 | A1 | 9/2016 | Ricci |
| 2017/0033567 | A1 | 2/2017 | Adamisin |
| 2017/0060298 | A1 | 3/2017 | Hwang et al. |
| 2017/0070078 | A1 | 3/2017 | Hwang et al. |
| 2017/0140333 | A1* | 5/2017 | Rinzler .................. H02J 50/10 |
| 2017/0143063 | A1 | 5/2017 | Huff et al. |
| 2017/0325518 | A1 | 11/2017 | Poupyrev et al. |
| 2018/0075734 | A1 | 3/2018 | Jurkuvenas et al. |
| 2018/0077124 | A1 | 3/2018 | Ramoutar |
| 2018/0083474 | A1 | 3/2018 | Rajamäki |
| 2018/0085283 | A1 | 3/2018 | Rahman |
| 2018/0259914 | A1 | 9/2018 | Chae |
| 2018/0262226 | A1 | 9/2018 | Erentok et al. |
| 2019/0009097 | A1* | 1/2019 | Hartley .................. H02J 50/90 |
| 2019/0059756 | A1 | 2/2019 | Rasmussen et al. |
| 2019/0123431 | A1 | 4/2019 | Ehman et al. |
| 2019/0131810 | A1* | 5/2019 | Lim ........................ H02J 7/342 |
| 2019/0393730 | A1 | 12/2019 | Wittenberg et al. |
| 2020/0015701 | A1 | 1/2020 | Wei et al. |
| 2023/0039159 | A1 | 2/2023 | Lynch |

FOREIGN PATENT DOCUMENTS

| | | |
|---|---|---|
| CN | 106911193 A | 6/2017 |
| CN | 107257150 A | 10/2017 |
| CN | 110575144 A | 12/2019 |
| EP | 2859839 A1 | 4/2015 |
| EP | 3116244 A1 | 1/2017 |
| EP | 3332698 A1 | 6/2018 |
| GB | 2553778 | 3/2018 |
| KR | 10-2017-0138007 A | 12/2017 |
| KR | 10-2017-0143063 A | 12/2017 |
| WO | WO 2015066094 | 5/2015 |
| WO | 2015/134654 A1 | 9/2015 |
| WO | WO 2017006152 | 1/2017 |
| WO | 2017/087862 A1 | 5/2017 |
| WO | WO 2017205671 | 11/2017 |
| WO | 2018/183038 A1 | 10/2018 |
| WO | 2019/168475 A1 | 9/2019 |
| WO | 2019/213114 A1 | 11/2019 |
| WO | 2020/033242 A1 | 2/2020 |
| WO | 2020/117559 A1 | 6/2020 |

OTHER PUBLICATIONS

GB Combined Search Report and Examination Report dated Mar. 26, 2020 of GB Application 1915658.7.
International Search Report and Written Opinion of PCT/GB2020/052722 dated Jan. 12, 2021.
2nd Examination Report of GB 2109912.2 dated Dec. 13, 2021.
3rd Examination Report of GB 2109912.2 dated Feb. 15, 2022.
4th Examination Report of GB 2109912.2 dated Mar. 21, 2022.
5th Examination Report of GB 2109912.2 dated May 30, 2022.
Air-Charge-Nike launches the Nike Adap tBB, first shoe with wireless charging capabilities (air-charge.com) Jan. 21, 2019 https://www.air-charge.com/news/204/19/Nike-launches-the-Nike-Adapt-BB-first-shoe-with-wireless-charging-capabilities.
Benedict,"JB14: RPM2 Power Meter Shoe Insole Inserts Measure Force Everywhere," IB14: RPM power Meter Shoe Insole Insearts Measure Force Everywhere—Bikerumor Posted on Oct. 19, 2014.
Flex Circuit Design Guide, Technical Specification FC302, Minco Flex Circuits, 2006 (30 pages).
Flex-Rigid Design Guide, Circuit Board Technology, Wurth Elektronik GmbH & Co. KG, Version 1.2, Mar. 2018 (8 pages).
GB Combined Search and Examinatio nReport of GB Application 20000860.3 dated Aug. 25, 2020.
GB Combined Search and Examination Report of GB2109912.2 dated Nov. 9, 2021.
International Search Report and Written Opinion received for PCT Patent Application No. PCT/GB2021/050113, dated Apr. 19, 2021, 14 pages.
Kaitsi et al.,"Clinical assessment of a non-invasive wearable MEMS pressure sensor array for monitoring of arterial pulse waveform, heartrate and detection of atrial fibrillation ,"Digital Medicine, Scripps Research Translational Institute, published on-line May 14, 2019.
Kaneko et al."Pulse wave measurement in human using piezoresistive cantilever on liquid," Conference Paper in Proceedings of the IEEE International Conference on Micro Electro Mechanical Systems (MEMS) Jan. 2015.
Mearian, "Wireless charging explained :What is it and how does it work?" Mar. 28, 2018.
Search Report of GB Application 2011930. 1 dated Jun. 23, 2021.
Sun et al.,"Wearable pulse wave monitoring system based on MEMS sensors,"Micromachines ,9 ,90 (2018) (10 pages).
Trenholm, Media Tek 361 smart shoe release date,news ,price and spec-CNET, Mar. 5, 2015.
Xu et al., Validation of a piezoelectric sensor array-based device for measurement of carotid-femoral pulse wave velocity: The Philips Prototype, Pulse ,5:161-168(2017).
U.S. Appl. No. 17/792,500, filed Jul. 13, 2022, Michael John Lynch.
"Bluetooth®—Bluetooth Core Specification v5.0" Dec. 6, 2016, pp. 2822
"The Qu Wireless Power Transfer System Power Class 0 Specification," Parts 1 and 2: Interface Definitions, Wireless Power Consortium, Version 1.2.3, Feb. 2017.
Chung, M.A. et al., "A Dual-Mode Antenna for Wireless Charging and Near Field communication," IEEE International Symposium on Antennas and Propagation & USNC/URSI National Radio Science Meeting, Jul. 19-24, 2015, pp. 1288-1289.
Clark, S., "NFC Forum unveils technical specification that lets IoT devices use a single antenna for both NFC and wireless charging," retrieved from https://www.nfcw.com/2019/01/16/359023/nfc-forum-technical-specification-single-antenna-nfc-and-wireless-charging/, Jan. 16, 2019.

(56) References Cited

OTHER PUBLICATIONS

Jimblom, "Bluetooth Basics," Published on sparkfun.com, archived on May 5, 2019 by the internet archive archive.org, available at here: https://web.archive.org/web/20190505203555/https://learn.sparkfun.com/tutorials/bluetooth-basics/how-bluetooth-works (2019).
Johns, B., "An Introduction to the Wireless Power Consortium standard and TI's compliant solution,"Analog Application Journal Texas Instruments Incorporated, (2011), pp. 10-12.
Schmallegger, NXP Semiconductors, Wireless charging, NFC or Qi for wearables? Jun. 26, 2019 Wireless Charging: NFC or Qi for Wearables?—Power Management—Elektroniknet.

\* cited by examiner

WEARABLE ARTICLE AND ELECTRONICS ARRANGEMENT FOR TRANSFERRING POWER

CROSS-REFERENCE TO RELATED APPLICATIONS

This application is a national stage application under 35 U.S.C. § 371 of International Application PCT/GB2020/052722, filed Oct. 28, 2020, which claims priority of GB Patent Application 1915658.7, filed Oct. 29, 2019. The disclosure of which are hereby incorporated by reference herein in their entireties.

BACKGROUND

The present invention is directed towards a wearable article, textile article and method for transferring power to other electronic apparatuses.

Wearable articles such as garments incorporate sensors designed to interface with a wearer of the article or the surrounding environment. The sensors may determine information such as the wearer's heart rate, rate of respiration, activity level, and body positioning. Such properties can be measured with a sensor assembly that includes a sensor for signal transduction and/or microprocessors for analysis.

US Patent Application Publication No. 2016/0071397 discloses a garment which incorporates batteries to power electronics coupled with the garment. A belt that stores energy and distributes it across the electrical devices on the wearer is employed. The belt may charge or power pants through conductive areas on the inside of the belt loops of the pants. Alternatively, the belt buckle may act as the connection for voltage to flow from the belt to pants or a shirt. Inductive charging may be employed. A transmitter coil in the belt may induce a voltage in a receiver coil found in the shirts and pants.

It is desirable to enable to provide improved mechanisms for transferring power between a wearable article and other electronic apparatuses.

SUMMARY

According to the present disclosure there is provided a wearable article, textile article, and method as set forth in the appended claims. Other features of the invention will be apparent from the dependent claims, and the description which follows.

According to a first aspect of the present disclosure, there is provided a wearable article. The wearable article comprises a power source and a processor. The processor is arranged to determine whether a power transfer condition is satisfied. In response to determining that the power transfer condition is satisfied, the processor is arranged to control the wearable article to transfer power from the power source to an electrical load of an external apparatus communicatively coupled to the wearable article.

Beneficially, the wearable article transfers power to an external apparatus. This enables power to be shared between the wearable article and other apparatuses such as other wearable articles. The wearable article may have a relatively large power source (e.g. with a relatively large power capacity). The wearable article may act as a charging hub for other apparatuses with smaller or no power sources or power sources with a limited amount of charge remaining. The wearable article is only arranged to transfer power if a power transfer condition is satisfied. This prevents or helps avoid the transfer of power in undesirable situations such as when the power source of the wearable article has only a limited amount of charge remaining.

The wearable article may further comprise a communicator. The communicator may be arranged to send and/or receive data to/from the external apparatus or another apparatus. The communicator may be arranged to receive the data from the external apparatus over a near-field communication protocol. The communicator may comprise a reader arranged to read a radio frequency identification (RFID) tag of the external apparatus so as to obtain the data from the external apparatus.

The wearable article may be arranged to receive data from the external apparatus, e.g. via the communicator of the wearable article. The wearable article may be arranged to transmit data to the external apparatus or another apparatus, e.g. via the communicator. The wearable article may be arranged to perform an action on the received data. The action may comprise one or more of storing the data in a memory; processing the data; and transmitting the data. In examples of the present disclosure, the external apparatus may transfer data to the wearable article if it is determined that the external apparatus does not have sufficient remaining charge to operate (e.g. for a predetermined duration).

The communicator may be arranged to receive identification information from the external apparatus. The identification information may relate to the identity of a user associated with the external apparatus. The processor may be arranged to determine from the identification information whether the power transfer condition is satisfied. The power transfer condition may be satisfied if the identification information identifies that the external apparatus is authorised to receive power from the wearable article. Advantageously, the wearable article communicates with the external apparatus and determines to transfer power based on the information received from the external apparatus.

In response to determining that the power transfer condition is not satisfied, the wearable article may not be controlled to transfer power to the electrical load of the external apparatus. In this way, power is not transferred to the external apparatus.

The identification information may comprise biometric information identifying a user associated with the external apparatus. The processor may be arranged to determine from the biometric information whether the user associated with the external apparatus is authorised to receive power from the wearable article. The processor may be arranged to determine from the biometric information whether the user associated with the external apparatus is the same as a user wearing the wearable article. The power transfer condition may be satisfied if the user associated with the external apparatus is the same as the user wearing the wearable article. The processor may be arranged to compare biometric information identifying the user wearing the wearable article to the biometric information identifying the user associated with the external apparatus to determine whether the user associated with the external apparatus is the same as a user wearing the wearable article. The biometric information identifying the user associated with the wearable article may be obtained from sensor data sensed by a sensor of the wearable article.

The communicator may be a wireless communicator operable to communicate the data wirelessly. The communicator may provide wireless communication capabilities for the wearable article and may enable the wearable article to communicate via one or more wireless communication protocols such as used for communication on: a wireless wide area network (WWAN), a wireless metro area network (WMAN), a wireless local area network (WLAN), a wireless personal area network (WPAN), a near field communication (NFC), and a cellular communication network. The cellular communication network may be a fourth generation (4G) LTE, LTE Advanced (LTE-A), fifth generation (5G), sixth generation (6G), and/or any other present or future developed cellular wireless network. The communicator may comprise a plurality of communicators. A first communicator of the wearable article may be provided for cellular communication and a separate communicator may be provided for short-range local communication over WLAN, WPAN, NFC, or Bluetooth®, Wi-Fi or any other electromagnetic RF communication protocol.

The power transfer condition may be satisfied if the power source has a remaining charge that is greater than a predetermined threshold. Advantageously, the wearable article may only transfer power to the external apparatus if the wearable article has sufficient remaining charge to enable the wearable article to function. The predetermined threshold may be selected as appropriate by the skilled person in the art based on factors such as the capacity of the power source. The predetermined threshold may be configurable by the user of the wearable article. The power transfer condition may be satisfied if the power source has a remaining charge that is sufficient to power the wearable article for a time that is greater than a predetermined threshold. Advantageously, the wearable article may only transfer power to the external apparatus if the wearable article has sufficient remaining charge to enable the wearable article to function for more than a predetermined period of time. The power transfer condition may be satisfied if the wearable article receives an authorisation command from the user to transfer power to the external apparatus. Advantageously, the wearable article may only transfer power to the external apparatus if the user wearing the wearable article approves the transfer of power. The wearable article may be arranged to determine any or a combination of the amount of power to transfer, the rate of power transfer, and the duration of the power transfer based on factors such as the remaining charge of the wearable article, the power demand of the wearable article on the power source, and the desired duration of operation of the wearable article.

The power transfer condition may be satisfied if a remaining charge of the external apparatus is less than a predetermined threshold. Advantageously, the wearable article may only transfer power to the external apparatus if the external apparatus needs the power to function. The wearable article may be arranged to receive power status level information from the external apparatus which indicates the remaining charge for the external apparatus. The communicator of the wearable article may be arranged to receive the power status level information. The wearable article may be arranged to determine whether to transfer power based on the received power status level information. The wearable article may be arranged to determine any or a combination of the amount of power to transfer, the rate of power transfer, and the duration of the power transfer from the power status level information and optionally any other information received from the external apparatus and/or derived from properties such as the remaining charge of the wearable article.

The wearable article may further comprise a power transmitter arranged to transfer power from the power source to the electrical load of the external apparatus. The power transmitter may be arranged to wirelessly transfer power from the power source to a power receiver of the external apparatus. The power transmitter may be arranged to transfer power from the power source to the power receiver over a contactless interface. The power transmitter may be arranged to inductively transfer power. The power transmitter may comprise a first resonator and the power receiver may comprise a second resonator. The power transmitter may comprise a power transmitter coil, and the power receiver may comprise a power receiver coil.

The power transmitter may be arranged to beam electromagnetic energy from the power source to a power receiver of the external apparatus. The power transmitter may be arranged to wirelessly beam electromagnetic energy in the form of microwaves. The microwaves may be focused microwaves. The wearable article may comprise a transducer. The transducer may be arranged to convert electrical energy from the power source into a beam of microwave energy to be transmitted by the power transmitter. The power transmitter may be arranged to beam electromagnetic energy over a first wireless network. The power transmitter may be a mobile transmitter. The mobile transmitter may be arranged to transmit data over a second wireless network. The second wireless network may be different from the first wireless network. The mobile transmitter may be a mobile transceiver. The mobile transceiver may be arranged to receive data from the external apparatus over the second wireless network. The second wireless network is a cellular network, a local area wireless network, or a personal area wireless network. The first wireless network is a cellular network, a local area wireless network, or a personal area wireless network. The wearable article may be arranged to locate the external apparatus (e.g. via communication with the external apparatus) and transmit a directed beam of electromagnetic energy to the external apparatus.

At least a component of the wearable article may be removable from the wearable article. The power source may be removable from the wearable article. The processor may be removable from the wearable article. Beneficially, this enables the power source and/or processor to be removed prior to washing of the wearable article for example. The power source and the processor may form an electronics module which is removable from the wearable article.

The wearable article may further comprise an interface element arranged to form a mechanical and/or electrical connection with the external apparatus. The interface element may form an electrical connection with the external apparatus so as to enable power to be transferred from the power source to the electrical load of the external apparatus. In this example, the interface element forms a physical coupling with the external apparatus such that a conductive connection is formed between the wearable article and the external apparatus. In effect, a wired connection may be considered as being formed between the wearable article and the external apparatus. The interface element may form a mechanical coupling. Beneficially, the mechanical coupling enables the wearable article to be securely coupled to the external apparatus so as to reduce the risk of or prevent the power coupling (e.g. conductive or inductive) between the wearable article and the external apparatus from breaking during the transfer of power between the wearable article and the external apparatus. The interface element may comprise a magnetic material. The magnetic material may be arranged to couple with magnetic material of the external apparatus to form the mechanical and/or conductive connection between the wearable article and the external apparatus. The interface element may comprise a fastener element. The fastener element may be arranged to couple with a corresponding fastener element of the external apparatus to form the mechanical and/or conductive connection between the wearable article and the external apparatus. The fastener may be a zipper, button, clasp, toggle, stud, snap fastener, popper, eyelet, buckle, tie or ribbon. The wearable article may comprise a conductive pathway which extends from the power source to the interface element.

The wearable article may further comprise a sensor or a plurality of sensors. The sensor may be arranged to sense one or more signals external to the wearer. The sensor may be any or a combination of a temperature sensor, a camera, a location tracking module such as a GPS module, and a chemical sensor. The sensor may be a biosensor arranged to measure one or more biosignals of a user wearing the wearable article. Here, "biosignal" may refer to any signal in a living being that can be measured and monitored. The term "biosignal" is not limited to electrical signals and can refer to other forms of non-electrical biosignals. The biosensor may be used for measuring one or a combination of bio-electrical, bioimpedance, biochemical, biomechanical, bioacoustics, biooptical or biothermal signals of the wearer. The bioelectrical measurements include electrocardiograms (ECG), electrogastrograms (EGG), electroencephalograms (EEG), and electromyography (EMG). The bioimpedance measurements include plethysmography (e.g., for respiration), body composition (e.g., hydration, fat, etc.), and electroimpedance tomography (EIT). The biomagnetic measurements include magnetoneurograms (MNG), magnetoencephalography (MEG), magnetogastrogram (MGG), magnetocardiogram (MCG). The biochemical measurements include glucose/lactose measurements which may be performed using chemical analysis of the wearer's sweat. The biomechanical measurements include blood pressure. The bioacoustics measurements include phonocardiograms (PCG). The biooptical measurements include orthopantomogram (OPG). The biothermal measurements include skin temperature and core body temperature measurements. The biosensor may comprise a radar unit. The wearable article may sense a combination of external signals and biosignals of the wearer.

The wearable article may comprise a Universal Integrated Circuit Card (UICC) that enables the wearable article to access services provided by a mobile network operator (MNO). The UICC may include at least a read-only memory (ROM) configured to store an MNO profile that the wearable article can utilize to register and interact with an MNO. The UICC may be in the form of a Subscriber Identity Module (SIM) card. The wearable article may have a receiving section arranged to receive the SIM card. In other examples, the UICC is embedded directly into a controller of the wearable article. That is, the UICC may be an electronic/embedded UICC (eUICC). A eUICC is beneficial as it removes the need to store a number of MNO profiles, i.e. electronic Subscriber Identity Modules (eSIMs). Moreover, eSIMs can be remotely provisioned to wearable articles. The wearable article may comprise a secure element that represents an embedded Universal Integrated Circuit Card (eUICC).

The external apparatus may be a second wearable article. The wearable article and/or the external apparatus may be a textile article. The textile article may include upholstery, such as upholstery that may be positioned on pieces of furniture, vehicle seating, as wall or ceiling décor, among other examples. The wearable article and/or the external apparatus may be a garment. The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, swimwear, wetsuit or drysuit. The garment/textile article may be constructed from a woven or a non-woven material. The garment/textile article may be constructed from natural fibres, synthetic fibres, or a natural fibre blended with one or more other materials which can be natural or synthetic. The yarn may be cotton. The cotton may be blended with polyester and/or viscose and/or polyamide according to the application. Silk may also be used as the natural fibre. Cellulose, wool, hemp and jute are also natural fibres that may be used in the garment/textile article. Polyester, polycotton, nylon and viscose are synthetic fibres that may be used in the garment/textile article. The garment may be a tight-fitting garment. Beneficially, a tight-fitting garment helps ensure that any sensors of the garment are held in contact with or in the proximity of a skin surface of the wearer. The garment may be a compression garment. The garment may be an athletic garment such as an elastomeric athletic garment.

The power source may comprise a plurality of power sources. The power source may be a battery. The battery may be a rechargeable battery. The battery may be a rechargeable battery adapted to be charged wirelessly such as by inductive charging. The power source may comprise an energy harvesting device. The energy harvesting device may be configured to generate electric power signals in response to kinetic events such as kinetic events performed by a wearer of the wearable article. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the wearable article. The energy harvesting device may be a thermoelectric energy harvesting device. The power source may be a super capacitor, or an energy cell.

There is also provided an electronics arrangement for the wearable article of the first aspect of the disclosure. The electronics arrangement comprises the power source and the processor. The processor is arranged to determine whether a power transfer condition is satisfied. In response to determining that the power transfer condition is satisfied, the processor is arranged to control the electronics arrangement to transfer power from the power source to an electrical load of an external apparatus communicatively coupled to the wearable article. The electronics arrangement may be arranged to be coupled to the wearable article or otherwise integrated into the wearable article. The electronics arrangement may be an electronics module.

According to a second aspect of the present disclosure, there is provided a method of transferring power from a wearable article to an external apparatus. The method comprises determining, by the wearable article, whether a power transfer condition is satisfied. In response to determining that the power transfer condition is satisfied, the method comprises transferring, by the wearable article, power from a power source of the wearable article to an electrical load of the external apparatus.

According to a third aspect of the present disclosure, there is provided a wearable article comprising a power source and an interface element. The interface element comprises magnetic material. The magnetic material is arranged to form an electrical connection with an external apparatus so as to enable power to be transferred from the power source to an electrical load of the external apparatus. The wearable article may comprise any or a combination of features described above in relation to the first aspect of the present disclosure.

Advantageously, the present disclosure provides a wearable article with an interface element comprising a magnetic material. The magnetic material facilitates the coupling of the wearable article to the external apparatus to provide an easy to use mechanism for transferring power from the wearable article to the external apparatus. Moreover, the magnetic material helps maintain the coupling between the wearable article and the external apparatus during the transfer of power even in situations where a user wearing the wearable article is moving.

According to a fourth aspect of the present disclosure, there is provided a method of transferring power from a wearable article to an external apparatus. The method comprises providing the wearable article of the third aspect of the present disclosure. The method comprises forming, by the wearable article, an electrical connection between the interface element of the wearable article and the external apparatus. The method comprises transferring, by the wearable article, power from the power source of the wearable article to an electrical load of the external apparatus via the electrical connection.

According to a fifth aspect of the present disclosure, there is provided an electronics module for a wearable article. The electronics module comprises a power source. The electronics module comprises a power transmitter arranged to beam electromagnetic energy from the power source to a power receiver of an external apparatus. The electronics module may comprise any or a combination of features described above in relation to the wearable article of the first or third aspect of the present disclosure. A wearable article comprising the electronics module is also provided.

Advantageously, the present disclosure provides a mechanism for beaming electromagnetic energy from the wearable article to the external apparatus. This enables the wearable article to transfer power over a distance and does not require a physical or close coupling between the wearable article and the external apparatus as may be required for conductive or inducting charging. Beneficially, the present disclosure enables a first wearable article such as footwear or a backpack which may have space for a larger power source to charge other wearable articles such as t-shirts, headwear or smartwatches which may be physically separated and spaced apart from the first wearable article.

According to a sixth aspect of the present disclosure, there is provided a method of transferring power from a wearable article to an external apparatus. The method comprises using a power transmitter of the wearable article to beam electromagnetic energy from the power source to a power receiver of the external apparatus.

According to a seventh aspect of the present disclosure, there is provided a garment. The garment comprises an electronics module comprising a processor and a first power source. The garment comprises a mounting arrangement. The garment comprises an electrically conductive pathway extending from the first power source to the mounting arrangement. The mounting arrangement is arranged to releasably retain a second power source. When the second power source is retained by the mounting arrangement, the first power source of the electronics module is arranged to receive power from the second power source via the electrically conductive pathway. The mounting arrangement may comprise a pocket. The garment may comprise any or a combination of features described above in relation to the wearable article of the first, third or fifth aspect of the present disclosure.

Advantageously, the garment provides a mounting arrangement to enable a power source to be releasably retained by the garment and thereby transfer power to the garment. This provides a convenient mechanism for charging a power source of the garment even when the garment is being worn.

According to an eighth aspect of the present disclosure, there is provided a garment. The garment comprises an electronics module mounting arrangement arranged to releasably retain an electronics module comprising a processor and a first power source. The garment comprises a second power source mounting arrangement arranged to releasably retain a second power source. The garment comprises an electrically conductive pathway extending from the first mounting arrangement to the second mounting arrangement. When the electronics module is retained by the electronics module mounting arrangement, and when the second power source is retained by the second power source mounting arrangement, the first power source of the electronics module is arranged to receive power from the second power source via the electrically conductive pathway. The second power source mounting arrangement may comprise a pocket. The garment may comprise any or a combination of features described above in relation to the wearable article of the first, third, fifth or seventh aspect of the present disclosure.

According to a ninth aspect of the present disclosure, there is provided a garment. The garment comprises a mounting arrangement. The garment comprises an electrically conductive pathway extending from the mounting arrangement. The electrically conductive pathway terminates in a power receiver at the mounting arrangement. The mounting arrangement may be arranged to releasably retain a power source comprising a power transmitter. When the second power source is retained by the mounting arrangement, the power receiver is arranged to wirelessly receive power from the power transmitter of the power source. The mounting arrangement may comprise a pocket. The garment may comprise any or a combination of features described above in relation to the wearable article of the first, third, fifth, seventh, or eighth aspect of the present disclosure.

According to a tenth aspect of the present disclosure, there is provided a wearable article. The wearable article comprises a power source; a processor; and a communicator. The processor is operable to: determine power status level information for the power source; determine, from the power status level information, whether to transfer data to an external apparatus; and in response to determining to transfer data, control the communicator to transfer data to the external apparatus. The wearable article may comprise any of the features described above in relation to the first, third, fifth, seventh, eighth or ninth aspect of the present disclosure.

Advantageously, the wearable article is arranged to determine whether to transfer power to an external apparatus based on a determined power status level for the wearable article. This enables the wearable article to transfer data to the external apparatus if the power status is low. This prevents or reduces the risk of the loss of data if the power source of the wearable article runs out of charge. In particular examples, the present disclosure enables the wearable article to dump data stored on the wearable article to an external device if the power status is low.

The data may comprise sensor data sensed by one or more sensors of the wearable article. The data may comprise the power status level information. The data may comprise identification information for the apparatus and/or a user associated with the wearable article. The data may comprise instructions for handling the data. The electronics arrangement may be arranged to receive power from a power source of the external apparatus such that power is transferred from the power source of the external apparatus to the power source of the wearable article.

The wearable articles referred to in the above aspects of the present disclosure may be any form of electronic device which may be worn by a user such as a smart watch, necklace, bracelet, or glasses. The wearable article may be a textile article.

The external apparatus referred to in the above aspects of the present disclosure may be a textile article, wearable article or garment but is not limited to these examples. The external apparatus may, for example, be any other form of electric device such as a user electronic device. The external apparatus may be any device capable of communicating with the wearable article over a wired or wireless communication network. The external apparatus may be a wireless device or a wired device. The wireless/wired device may be a mobile phone, tablet computer, gaming system, MP3 player, point-of-sale device. A wireless device is intended to encompass any compatible mobile technology computing device that connects to a wireless communication network, such as mobile phones, mobile equipment, mobile stations, user equipment, cellular phones, smartphones, handsets or the like, wireless dongles or other mobile computing devices. The wireless communication network is intended to encompass any type of wireless network such as mobile/cellular networks used to provide mobile phone services. The external apparatus may be a medical device. The external apparatus may be a skin surface sensor. Skin surface sensors will be understood as referring to a sensor that is adhered or otherwise attached to the skin. The external apparatus may be an implantable medical device.

The present disclosure is not limited to transferring power between wearable articles. That is, while the above examples generally refer to wearable article the aspects of the present disclosure may apply to textile articles which may not necessarily be wearable. The textile article may include upholstery, such as upholstery that may be positioned on pieces of furniture, vehicle seating, as wall or ceiling décor, among other examples

BRIEF DESCRIPTION OF THE DRAWINGS

Examples of the present disclosure will now be described with reference to the accompanying drawings, in which.

DETAILED DESCRIPTION

Figure 1:
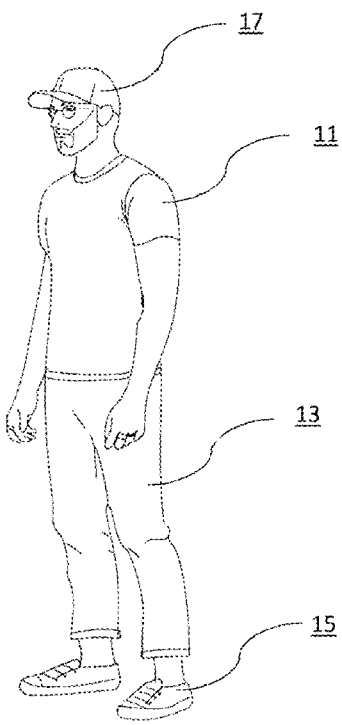
FIG. 1 shows an example system comprising wearable articles according to aspects of the present disclosure.
Figure 2:
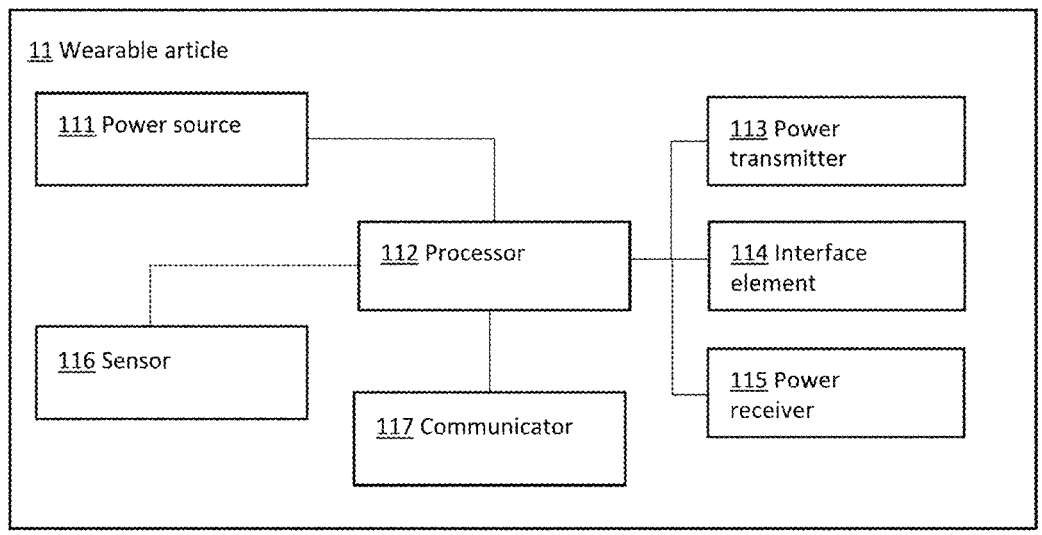
FIG. 2 shows a simplified schematic diagram of an example wearable article according to aspects of the present disclosure.
Figure 3:
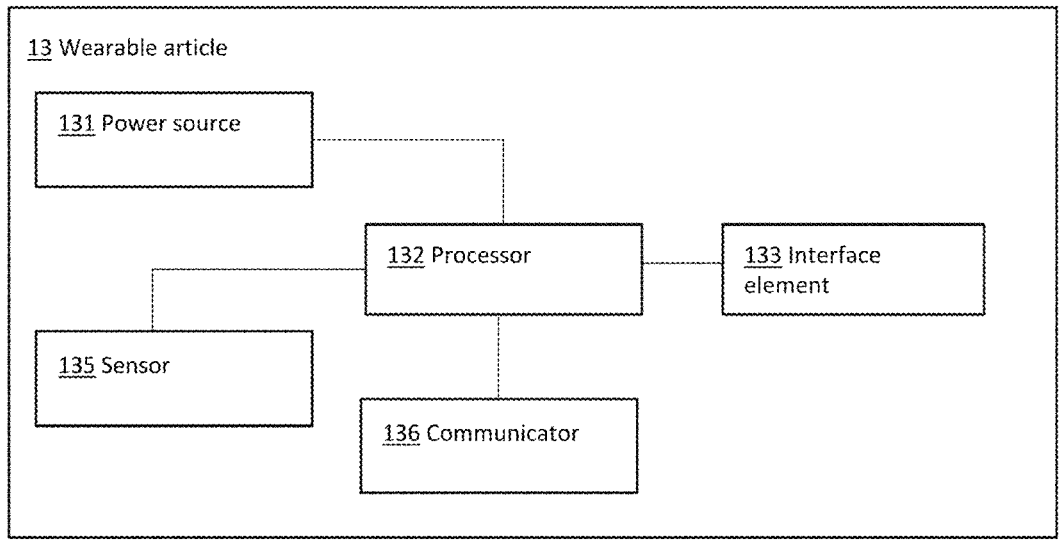
FIG. 3 shows a simplified schematic diagram of another example wearable article according to aspects of the present disclosure.
Figure 4:
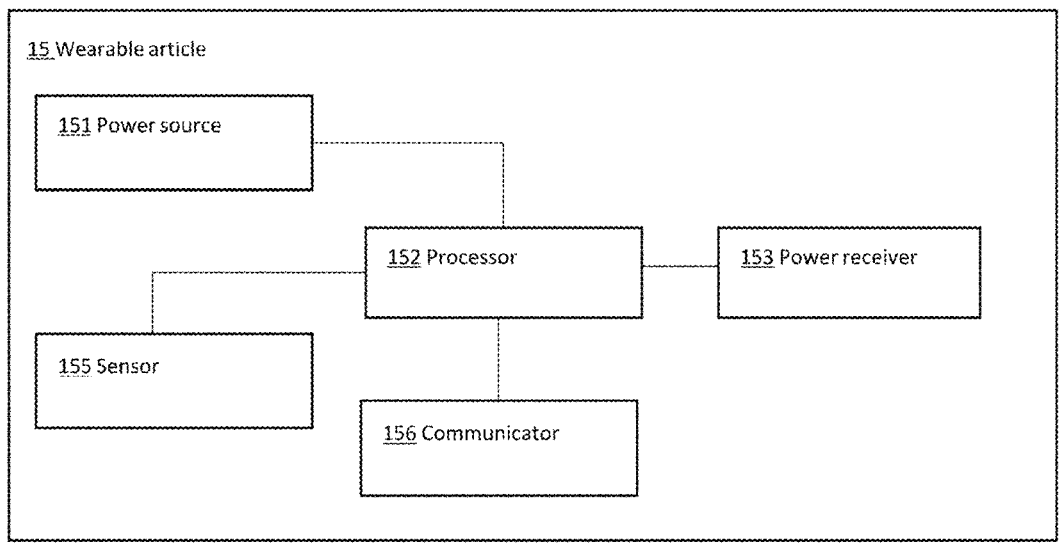
FIG. 4 shows a simplified schematic diagram of yet another example wearable article according to aspects of the present disclosure.
Figure 5:
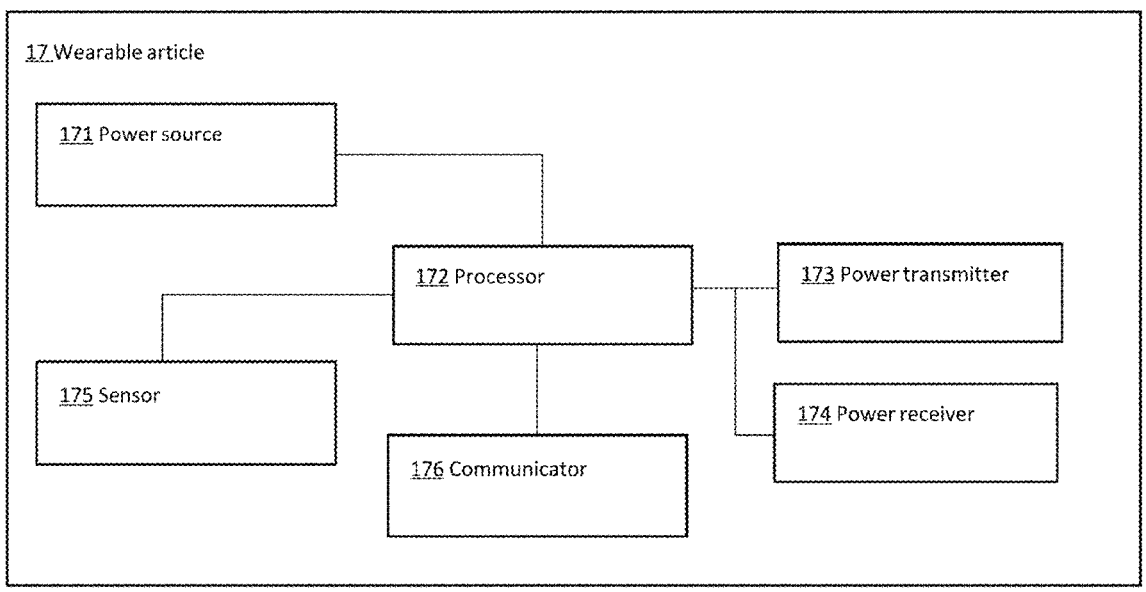
FIG. 5 shows a simplified schematic diagram of yet another example wearable article according to aspects of the present disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

Referring to FIGS. 1 through 5, there is shown a user wearing wearable articles 11, 13, 15, 17. The wearable articles 11, 13, 15, 17 include a first wearable article 11 the form of a t-shirt 11, a second wearable article 13 in the form of a pair of trousers 13, a third wearable article 15 in the form of footwear 15, and a fourth wearable article 17 in the form of a hat 17. The first wearable article 11 is arranged to transfer power from the power source 111 to the power sources 131, 151, 171 of the second, third and fourth wearable articles 13, 15, and 17. The wearable articles 11, 13, 15, 17 comprise electronics arrangements. Electronics arrangement refer to a collection of electronics components that may be able to interact with one another. Some or all of the electronics components may be provided together in an electronics module.

The first wearable article 11 comprises a first power source 111, a processor 112, power transmitter 113, interface element 114, power receiver 115, sensor 116 and communicator 117. A power bus (not shown) extends from the power source 111 to the power transmitter 113, interface element 114, and power receiver 115 to enable power to be transferred from the first power source 111 to power sources of other wearable articles 13, 15, 17 and vice versa, The power source 111, power transmitter 113, interface element 114, and power receiver 115 are communicatively connected to the processor 112 which is arranged to selectively control these elements.

The first wearable article 11 is arranged to form a communicative coupling with the wearable articles 13, 15, 17 so as to transfer power from the first power source 111 to second power sources of the wearable articles 13, 15, 17. The communicative coupling is formed via one or a combination of the power transmitter 113 and the interface element 114. Generally, the power transmitter 113 is used to transfer power wirelessly such as inductively or over an air interface, and the interface element 114 is used to transfer power over a wired interface by forming a conductive pathway between the power source 111 of the wearable article 11 and a power source of another wearable article 13, 15, 17.

In some examples, the power transmitter 113 is arranged to inductively transfer power. In these examples the power transmitter 113 comprises one or more transmitter elements such as transmitter coils and the power receiver of the other wearable article 13, 15, 17 comprises one or more receiver elements such as receiver coils. The transmitter elements may be located at different positions in the wearable article 11 or may be arranged together.

The power receiver 115 of the first wearable article 11 is arranged to form a communicative coupling with the wearable articles 13, 15, 17 or another article (not shown) so as to receive power for charging the first power source 111. In one example, the power receiver 115 may receive power from the footwear 15 as footwear 15 generally have sufficient space for the storage of a relatively large power source. The power receiver 115 may receive power from a backpack or other device for example.

The sensor 119 is arranged to sense data and the communicator 121 is arranged to transmit or receive data from an external device such as the wearable articles 13, 15, 17. The sensor 119 and the communicator 121 are controlled by the processor 113. The power transmitter 113 and the power receiver 115 may be provided as a single unit which may be referred to as a power transceiver 113, 115.

The second wearable article 13 comprises a power source 131, processor 132, interface element 133, sensor 135, and communicator 136.

The first wearable article 11 is conductively connected to the second wearable article 13 to enable power to be transferred from the first wearable article 11 to the second wearable article 13. The interface element 114 of the first wearable article 11 forms a conductive and mechanical connection with the interface element 133 of the second wearable article 13 so as to enable power to be transferred from the first power source 111 to the second power source 131 of the second wearable article 13. The interface element 114 forms a physical coupling with the second wearable article 13 such that a conductive connection is formed between the first wearable article 11 and the second wearable article 13. In effect, a wired connection is formed between the first wearable article 11 and the second wearable article 13.

The interface element 114 is provided in the form of a magnetic material provided on an inside lower surface of the first wearable article 11 (e.g. the skin facing surface of the t-shirt 11). A conductive pathway extends from the first power source 111 to the interface element 114 of the first wearable article 11.

The second wearable article 13 comprises an interface element 133 which is arranged to connect with the interface element 114 of the first wearable article 11. A conductive pathway extends from the second power source 131 to the interface element 133 of the second wearable article 13. Thus, when the interface element 114 of the first wearable article 11 is connected to the interface element 133 of the second wearable article 13, the first power source 111 is in conductive connection with the second power source 131. The interface element 133 is provided in the form of a magnetic material provided on an outer upper surface of the second wearable article 13 (e.g. the outside facing surface of the trousers 13). In this way, when the user wears t-shirt 11, the t-shirt 11 drapes over the trousers 13 which results in the interface elements 114, 133 being magnetically attracted towards one another to form a conductive and mechanical coupling. It will be appreciated that the interface element 114 may be provided on an outside surface of the first wearable article 11 and the interface element 133 may be provided on an inside surface of the second wearable article 13 if, for example, the t-shirt 11 is desired to be tucked into the trousers 13. The use of a magnetic material for the interface element 114, 133 is beneficial as it helps ensure that a conductive coupling is formed with minimal effort from the user. The magnetic material may also enhance alignment when wireless (e.g. inductive) charging is performed. For example, magnetic material such as permanent magnets may be placed in the vicinity of the power transmitter 113 of the wearable article 11 and corresponding ferromagnetic material may be placed within or near the power receiver of the other wearable article 13, 15, 17. Other forms of interface element such as fasteners may help temporarily align the power transmitter of the wearable article 11 with the power receiver of the other wearable article 13, 15, 17 to facilitate charging.

The third wearable article 15 comprises a power source 151, processor 152, power receiver 153, sensor 155 and communicator 156. The fourth wearable article 17 comprises a power source 171, processor 172, power transmitter 173, power receiver 174, sensor 175 and communicator 176.

The first wearable article 11 is communicatively connected to the third and fourth wearable articles 15, 17 so as to enable power to be transferred from the first wearable article 11 to the third and fourth wearable articles 15, 17 over a wireless network. In particular, the power transmitter 113 of the first wearable article 11 is arranged to wirelessly transmit power from the first power source 111 to the power sources 151, 171 of the third wearable article 15 and the fourth wearable article 17. The third wearable article 15 and the fourth wearable article 17 comprise power receivers 153, 174 arranged to receive power transmitted by the first wearable article 11

The first wearable article 11 is therefore able to transfer power to the third and fourth wearable articles 15, 17 wirelessly without a physical conductive connection between the articles 15, 17. The power transmitter 113 of the first wearable article 11 is driven by electric power from the first power source 111. The power transmitter 113 generates a time-varying electromagnetic field, which transmits power wirelessly to the power receiver 153, 154 of the third or fourth wearable article 15, 17.

In this example, the third and fourth wearable articles 15, 17 are physically separated from the wearable article 11 by a relatively large air gap which generally means that inductive charging is not feasible. To charge the third and further wearable articles 15, 17, the power transmitter 113 of the first wearable article 11 beams the electromagnetic energy from the wearable articles 15, 17.

The beaming of energy may be performed using microwaves and in particular focused microwaves. In these examples, the first wearable article 11 may comprise a transducer (not shown) which is arranged to convert electrical energy from the power source 11 into a focused beam of microwave energy that is transmitted by the power transmitter 113. The power transmitter 113 may comprise one or a plurality of antennas for the purpose of transmitting the microwave energy. The first wearable article 11 may have information relating to the location of the wearable articles 15, 17 so that the beamed energy is directed towards the wearable articles 15, 17. This information may be obtained through RF communication between the wearable article 11 and the wearable articles 15, 17 or by other means. The wearable article 11 may be pre-programmed to determine the locations of the wearable articles 15, 17 based on factors such as the type of wearable articles 15, 17. For example, if the wearable article 11 is able to determine that the wearable article 15 is an item of footwear, the wearable article 11 may be able to determine to beam energy in a downwards direction. Another example of the beaming of energy involves the use of ultrasonic waves rather than microwaves.

The beaming of energy may be performed over a wireless network. In this arrangement, the power transmitter 113 may be arranged to transmit power over a first wireless network which may, for example, be a short-range wireless network such as a wireless personal area network (PAN). The power transmitter 113 may be part of or may be the communicator 117. That is, the transmitter of the communicator 117 may be the power transmitter 113. The power transmitter 113 may be a mobile transmitter 113 arranged to transmit power over a wireless network such as a cellular network. Beneficially, the same mobile transmitter 113 used to transfer power may be arranged to transmit and/or receive data to the wearable articles 15, 17 or other external devices. Power may be transferred over a first wireless network and data may be transferred over a second wireless network which may be different to the first wireless network. The second wireless network may be a cellular network. In preferred implementations, the mobile transmitter 113 is a mobile transceiver 113, 115 arranged to transmit and receive data and power over the wireless networks. The mobile transceiver 113 may transmit and/or receive data over a cellular network and may transmit and/or receive power over a personal area network. The power may be transmitted in the form of pulsed RF energy, continuous RF energy, intermittent RF energy, and/or multiband RF energy.

In some implementations, the wearable article 11 is arranged to transfer power whenever the wearable article 11 is brought into communication with another of the wearable articles 13, 15, 17. In preferred implementations, however, the wearable article 11 performs an additional determination step before transferring power. This determination step is beneficial as it ensures that power is transferred only when certain conditions are met. This helps reduce unnecessary power drain for the wearable article 11 and helps avoid the transfer of power to apparatuses without the user's authorisation.

In some examples. the processor 112 of the wearable article 11 is arranged to determine whether a power transfer condition is satisfied. In response to determining that the power transfer condition is satisfied, the processor 112 is arranged to control the wearable article 11 to transfer power from the power source 111 to one of the other wearable articles 13, 15, 17. The power transfer condition may relate to information received from the wearable article 13, 15, 17. The information may relate to the identity of the wearable article 13, 15, 17, the identity of a user wearing the wearable article 13, 15, 17, and/or an available charge level of the wearable article 13, 15, 17. The processor 112 of the wearable article 11 may determine whether the power transfer condition is satisfied based on information received from the wearable article 13, 15, 17.

In some examples, the communicator 117 of the wearable article 11 receives identification information from the wearable article 13, 15, 17. The processor 112 determines from the identification information whether the power transfer condition is satisfied.

In some examples, the power transfer condition is satisfied if the identification information identifies that the wearable article 13, 15, 17 is authorised to receive power from the wearable article 11. This may mean that the wearable article 13, 15, 17 is associated with the user wearing the wearable article 11 or with another user that is authorised by the user wearing the wearable article 11. For example, the user wearing the wearable article 11 may authorize family members or friends to be able to receive power from the wearable article 11. The identification information may be biometric information identifying a user associated with the wearable article 13, 15, 17. The biometric information may be sensed by a sensor of the wearable article 13, 15, 17. The processor 112 is arranged to determine from the biometric information whether the user associated with the wearable article 13, 15, 17 is authorised to receive power from the wearable article 11. The processor 112 may make the determination by comparing the biometric information identifying the user wearing the wearable article 11 to the biometric information identifying the user associated with the wearable article 13, 15, 17 to determine whether the user associated with the wearable article 13, 15, 17 is the same as a user wearing the wearable article 11.

Before power is transferred, the wearable article 11 may first determine how much (if any) power it may transfer. This determination may be based on several metrics. One example metric is whether the power source 111 has a remaining charge that is greater than a predetermined threshold. This means that the processor 112 determines whether the power source 111 has sufficient spare power to be transferred to the wearable article 13, 15, 17. Another example metric is whether the power source 111 has a remaining charge that is sufficient to power the wearable article 11 for a time that is greater than a predetermined threshold. This may mean that the processor 112 estimates the remaining battery life of the wearable article 11 and determines whether to transfer power based on this estimate. For example, if the wearable article 11 has less than one hour of battery life remaining, the processor 112 may determine not to transfer power to the wearable article 13, 15, 17. Of course, other time durations are within the scope of the present disclosure. Another example metric is whether the wearable article 11 has received an authorisation command from the user to transfer power to the wearable article 13, 15, 17. The user may be prompted by a user electronic device in communication with the wearable article 11 or the wearable article 11 itself to authorize the transfer of power. The user may be presented with information indicating amongst other things the remaining batter life of the wearable article 11. The user may authorize the transfer of power via a user input, gesture, or voice command amongst others. Another example metric is whether a remaining charge of the wearable article 13, 15, 17 is less than a predetermined threshold. This may mean that the wearable article 11 receives power status level information from the wearable article 13, 15, 17 which indicates the remaining charge for the wearable article 13, 15, 17. If the wearable article 13, 15, 17 has sufficient remaining charge then the wearable article 11 may determine not to transfer power.

In some implementations, the wearable article 13, 15, 17 is arranged to transfer data to the wearable article 11 based on a determined power status level information of the wearable article 13, 15, 17. In these examples, the processor 132, 152, 172 of the wearable article 13, 15, 17 determines power status level information for the power source 131, 151, 171. The processor 132, 152, 172 then determines, from the power status level information, whether to transfer data to the wearable article 11. In response to determining to transfer data, the processor 132, 152, 172 controls the communicator 136, 156, 176 to transfer data to the wearable article 11. The power status level information may relate to the remaining charge for the power source 131, 151, 171. The processor 132, 152, 172 may determine to transfer data if the remaining charge is less than a predetermined threshold or if the remaining charge is only sufficient to power the wearable article 13, 15, 17 for a time that is less than a predetermined threshold.

In example implementations, the data comprises sensor data sensed by one or more sensors 135, 155, 175 of the wearable article 13, 15, 17. The sensor data may be raw or processed sensor data. Transferring sensor data to the wearable article 11 provides the wearable article 13, 15, 17 with a mechanism to offload and backup sensor data. This protects against the data being lost if, for example, the wearable article 13, 15, 17 runs out of power and is shut down. The data may further comprise instructions for handling the sensor data. The instructions may relate to how to process the sensor data. This may enable the wearable article 13, 15, 17 to offload some of the processing tasks to the wearable article 11 so as to help conserve the battery life of the wearable article 13, 15, 17. The data may additionally or separately comprise the power status level information and/or identification information for the apparatus and/or a user associated with the wearable article 13, 15, 17.

Figure 6:
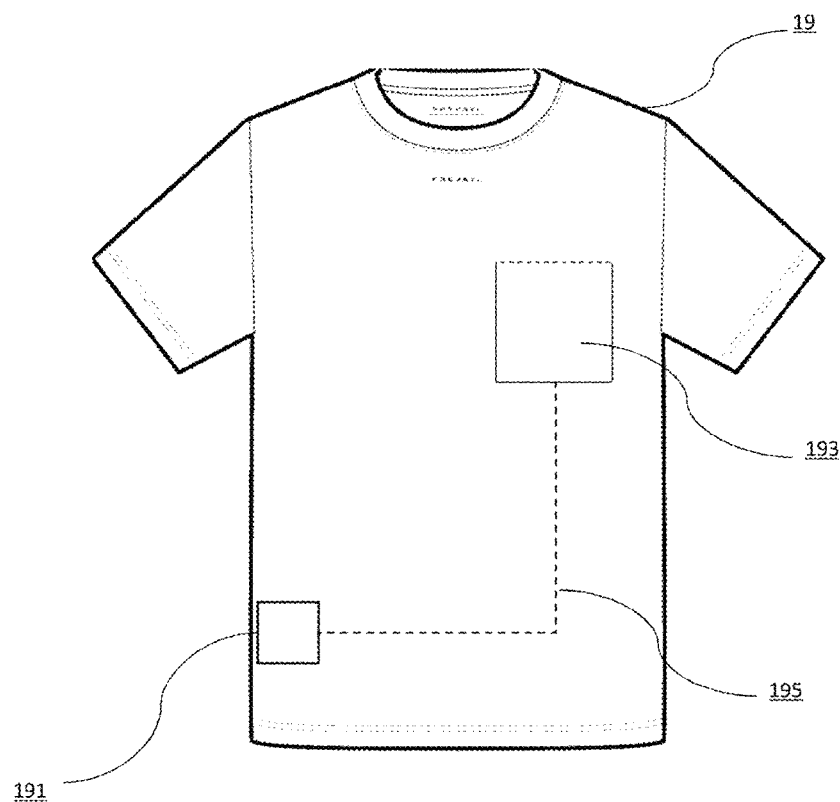
FIG. 6 shows a simplified schematic diagram of an example garment according to aspects of the present disclosure.

Referring to FIG. 6, there is shown an example garment 19 according to aspects of the present disclosure. The garment 19 is in the form of a T-shirt. The garment 19 comprises an electronics module 191 comprising a processor and a first power source. The electronics module 191 may be the same as or similar to the electronics arrangements described above in relation to wearable articles 11, 13, 15, 17. The garment further comprises a mounting arrangement 193 which, in this example, is in the form of a pocket positioned 193 on the outside surface of the garment 19. The pocket 193 has an opening at the top. The garment 19 further comprises an electrically conductive pathway 195 which extends from the first power source of the electronics module 191 to the mounting arrangement 193. The electrically conductive pathway 195 may be hidden in the garment 19 and may not be visible from an outside surface of the garment 19.

The mounting arrangement 193 is arranged to releasably retain a second power source (not shown). This may mean that the second power source is able to be positioned within the pocket 193. The second power source may be a user electronic device such as a mobile phone or a power bank. When the second power source is retained by the mounting arrangement 193, the first power source and the second power source are brought into electrical communication via the electrically conductive pathway. This enables the electronics module 191 to receive power from the second power source via the electrically conductive pathway 195 or vice versa. In this way, the second power source may be used to charge the power source of the electronics module 191.

Figure 7:
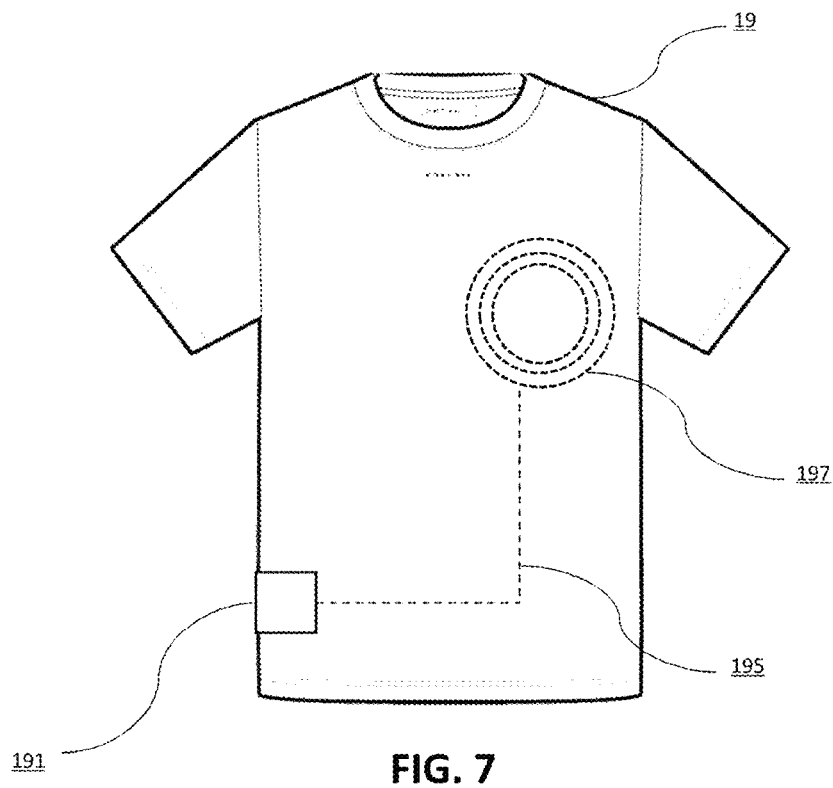
FIG. 7 shows a sectional view of the garment shown in FIG. 6.

Referring to FIG. 7, there is shown a sectional view of the garment 19 in FIG. 6. The sectional view shows that a power receiver 197 comprising one or more coils is provided within the garment 19 in the vicinity of the mounting arrangement. The electrically conductive pathway 195 terminates in the power receiver 197 which means that the electrically conductive pathway 195 electrically connects the electronics module 191 to the power receiver 197. The second power source comprises a power transmitter comprising one or more coils. When the second power source is retained by the mounting arrangement 193, an inductive coupling is formed between the power receiver 197 and the power transmitter which enables the second power source to inductively transfer power to the first power source of the electronics module 191.

In some examples, the mounting arrangement 193 comprises an interface element arranged to form a mechanical and/or electrical connection with the second power source. The interface element may provide a mechanical connection to help hold the second power source in a fixed position relative to the power receiver 197. This may enhance the transfer of power from the second power source to the first power source by helping to ensure that that an inductive coupling is formed and maintained. The interface element may form an electrical connection with the second power source so as to enable power to be transferred from the first power source to the second power source. The electrical connection may be separate to or in addition to the inductive coupling. That is, rather than just inductively charging the second power source, the interface element may form a physical conductive connection between the first and second power source so as to enable the transfer of power.

In some implementations, the interface element comprises a magnetic material. The magnetic material is arranged to couple with magnetic material of the second power source to form the mechanical and/or conductive connection with the second power source.

In some implementations, the interface element comprises a fastener element. The fastener element is arranged to couple with a corresponding fastener element of the second power source to form the mechanical and/or conductive connection with the second power source.

In some implementations, the electronics module 191 is removable from the garment 19. In these implementations, the garment may comprise a second mounting arrangement (not shown). The second mounting arrangement may be arranged to releasably retain the electronics module.

Figure 8:
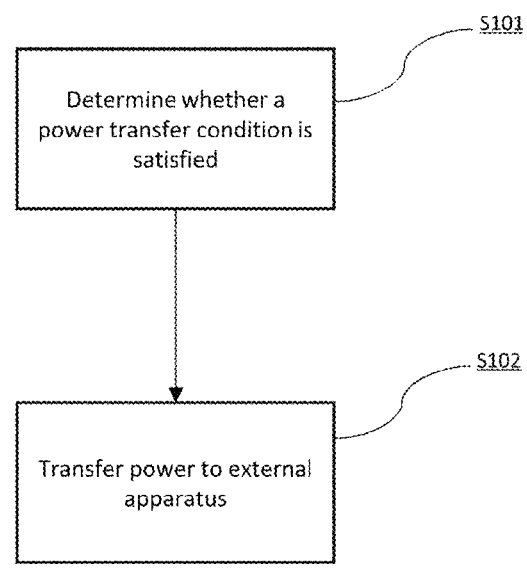
FIG. 8 shows a flow diagram for an example method according to aspects of the present disclosure.

Referring to FIG. 8, there is shown an example method of transferring power from a wearable article to an external apparatus according to aspects of the present disclosure. Step S101 of the method comprises determining, by the wearable article, whether a power transfer condition is satisfied. In response to determining that the power transfer condition is satisfied, step S102 of the method comprises transferring, by the wearable article, power from the power source to an electrical load of the external apparatus.

Figure 9:
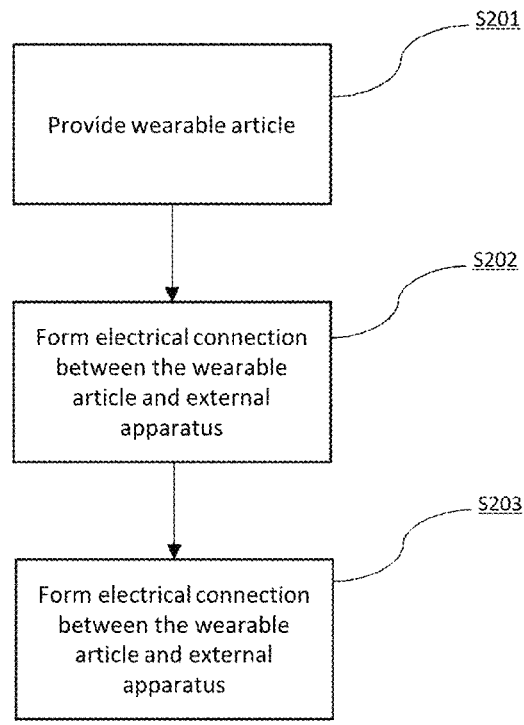
FIG. 9 shows a flow diagram for another example method according to aspects of the present disclosure.

Referring to FIG. 9, there is shown an example method of transferring power from a wearable article to an external apparatus. Step S201 of the method comprises providing a wearable article comprising: a power source; and an interface element comprising magnetic material, wherein the magnetic material is arranged to form an electrical connection with an external apparatus so as to enable power to be transferred from the power source to an electrical load of the external apparatus. Step S202 of the method comprises forming, by the wearable article, an electrical connection between the interface element of the wearable article and the external apparatus. Step S203 of the method comprises transferring, by the wearable article, power from a first power source of the wearable article to an electrical load of the external apparatus via the electrical connection.

Figure 10:
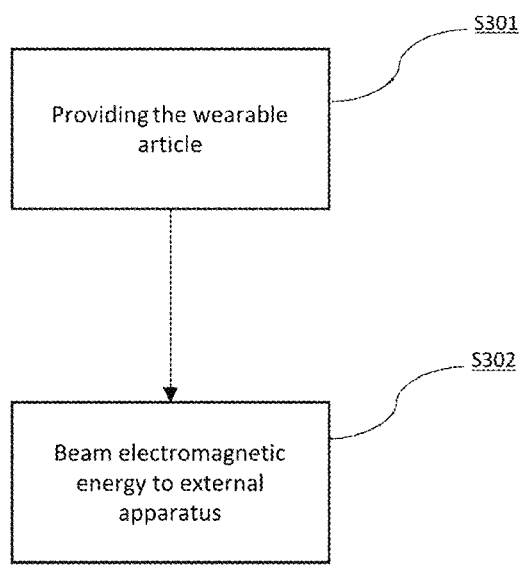
FIG. 10 shows a flow diagram for yet another example method according to aspects of the present disclosure.

Referring to FIG. 10, there is shown an example method of transferring power from a wearable article to an external apparatus. The method comprises providing the wearable article. The method comprises using a power transmitter of the wearable article to beam electromagnetic energy from the power source to a power receiver of the external apparatus.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A wearable article comprising:
    a power source;
    a processor; and
    a wireless power transmitter;
    wherein the processor is arranged to determine whether a power transfer condition is satisfied, and, in response to determining that the power transfer condition is satisfied, the processor is arranged to control the wireless power transmitter to wirelessly transfer power from the power source to an electrical load of an external apparatus communicatively coupled to the wearable article,
    wherein the wearable article further comprises a fastener element, the fastener element comprising a clasp arranged to form a mechanical connection with the external apparatus.

2. The wearable article as claimed in claim 1, further comprising a communicator arranged to receive identification information from the external apparatus, wherein the processor is arranged to determine from the identification information whether the power transfer condition is satisfied.

3. The wearable article as claimed in claim 2, wherein the processor is arranged to determine that the power transfer condition is satisfied when the identification information identifies that the external apparatus is authorized to receive power from the wearable article.

4. The wearable article as claimed in claim 2, wherein the identification information relates to the identity of a user associated with the external apparatus.

5. The wearable article claimed in claim 4, wherein the identification information comprises biometric information identifying a user associated with the external apparatus.

6. The wearable article as claimed in claim 5, wherein the processor is arranged to determine from the biometric information whether the user associated with the external apparatus is authorized to receive power from the wearable article.

7. The wearable article as claimed in claim 6, wherein the processor is arranged to determine from the biometric information whether the user associated with the external apparatus is the same as a user wearing the wearable article, and wherein the processor is arranged to determine that the power transfer condition is satisfied when the user associated with the external apparatus is the same as the user wearing the wearable article.

8. The wearable article as claimed in claim 7, wherein the processor is arranged to compare biometric information identifying the user wearing the wearable article to the biometric information identifying the user associated with the external apparatus to determine whether the user associated with the external apparatus is the same as a user wearing the wearable article, wherein the biometric information identifying the user associated with the wearable article is obtained from sensor data sensed by a sensor of the wearable article.

9. The wearable article as claimed in claim 2, wherein the communicator is arranged to receive the identification information over a near-field communication protocol.

10. The wearable article as claimed in claim 1, wherein the processor is arranged to determine that the power transfer condition is satisfied when the wearable article receives an authorization command from a user to transfer power to the external apparatus.

11. The wearable article as claimed in claim 1, wherein the processor is arranged to determine that the power transfer condition is satisfied when a remaining charge of the external apparatus is less than a predetermined threshold, the wearable article is arranged to receive power status level information from the external apparatus which indicates the remaining charge for the external apparatus.

12. The wearable article as claimed in claim 1, wherein the wearable article is arranged to receive data from the external apparatus, wherein the wearable article is arranged to perform an action on the received data, wherein the action comprises one or more of storing the data in a memory; processing the data; and transmitting the data.

13. The wearable article as claimed in claim 1, wherein the external apparatus is a further wearable article.

14. An apparatus comprising:
an electrical load;
a wireless power receiver; and
a communicator,
wherein the communicator is arranged to transmit identification information and/or power status level information to a wearable article that is communicatively coupled to the apparatus, and
wherein the wireless power receiver is arranged to receive power from a power source of the wearable article such that power is transferred from the power source to the electrical load,
wherein the apparatus is arranged to mechanically couple to the wearable article by a fastener element comprising a clasp.

15. The apparatus as claimed in claim 14, wherein the apparatus is a wearable article.

16. The apparatus as claimed in claim 15, wherein the wearable article comprises a sensor.

17. The apparatus as claimed in claim 16, wherein the sensor comprises an optical biosensor.

18. A method of transferring power from a wearable article to an external apparatus, the method comprising:
mechanically coupling, by a fastener element comprising a clasp, the wearable article to the external apparatus;
determining, by the wearable article, whether a power transfer condition is satisfied; and
in response to determining that the power transfer condition is satisfied, wirelessly transferring, by the wearable article, power from a power source to an electrical load of the external apparatus.

19. The wearable article as claimed in claim 1, wherein:
the wearable article is arranged to receive identification information from the external apparatus mechanically connected to the fastener element, the identification information identifying whether the external apparatus is authorized to receive power from the wearable article;
the power transfer condition is satisfied when the identification information identifies that the external apparatus is authorized to receive power from the wearable article; and
the processor is further arranged to, in response to determining that the power transfer condition is not satisfied when the identification information identifies that the external apparatus is not authorized to receive power from the wearable article, control the wireless power transmitter to not wirelessly transfer power to the external apparatus.

20. The method as claimed in claim 18, further comprising:
receiving, by the wearable article, identification information from the external apparatus mechanically connected to the fastener element, the identification information identifying whether the external apparatus is authorized to receive power from the wearable article;
determining, by the wearable article, that the power transfer condition is satisfied when the identification information identifies that the external apparatus is authorized to receive power from the wearable article; and
in response to determining that the power transfer condition is not satisfied when the identification information identifies that the external apparatus is not authorized to receive power from the wearable article, control a wireless power transmitter of the wearable article to not wirelessly transfer power to the external apparatus.

* * * * *